United States Patent [19]

Stam

[11] 4,024,130

[45] May 17, 1977

[54] PROCESS FOR THE MANUFACTURE OF ALKALI METAL SALTS OF 6-[2-PHENYL-2-(IMIDOYLAMINOALK-ANOYLAMINO)ACETAMIDO]PENICIL-LANIC ACIDS

[75] Inventor: John G. Stam, Waterford, Conn.

[73] Assignee: Pfizer Inc., New York, N.Y.

[22] Filed: Mar. 31, 1975

[21] Appl. No.: 563,846

[52] U.S. Cl. .......................................... 260/239.1
[51] Int. Cl.² ..................................... C07D 499/70
[58] Field of Search ................................ 260/239.1

[56] References Cited

UNITED STATES PATENTS 3,669,957  6/1972  Robinson et al. .............. 260/239.1

FOREIGN PATENTS OR APPLICATIONS

| 803,094 | 2/1974 | Belgium | 260/239.1 |
| 810,266 | 7/1974 | Belgium | 260/239.1 |
| 1,060,034 | 2/1967 | United Kingdom | 260/239.1 |
| 1,128,235 | 9/1968 | United Kingdom | 260/239.1 |

Primary Examiner—Gerald A. Schwartz
Attorney, Agent, or Firm—Connolly and Hutz

[57] ABSTRACT

An improved process for the manufacture of alkali metal salts of 6-[2-phenyl-2-(imidoylaminoalkanoylamino)acetamido]penicillanic acids.

8 Claims, No Drawings

PROCESS FOR THE MANUFACTURE OF ALKALI METAL SALTS OF 6-[2-PHENYL-2-(IMIDOYLAMINOALKANOYLAMINO)ACETAMIDO]PENICILLANIC ACIDS

BACKGROUND OF THE INVENTION

This invention relates to a novel, convenient and economic process for producing alkali metal salts of certain penicillanic acid derivatives. More particularly, it relates to the production of alkali metal salts of 6-[2-phenyl-2-(imidoylaminoalkanoylamino)acetamido]-penicillanic acids, a class of broad spectrum antibacterial agents especially useful against gram-negative microorganisms.

Belgian Pat. Nos. 803,094 and 810,266, granted February 1, 1974 and July 29, 1974, respectively, describe certain 6-[2-aryl-2-(imidoylaminoalkanoylamino)acetamido]penicillanic acids and various salts thereof, including alkali metal salts, which are valuable broad spectrum antibiotics, especially against gram-negative micro-organisms. The methods for alkali metal salt formation described therein comprise reacting the appropriate penicillanic acid derivative with an appropriate alkali metal salt (hydroxide, carbonate, bicarbonate, hydride, alkoxide) in an aqueous or non-aqueous medium and recovering the salt by lyophilization.

The relatively high polar nature of the herein described penicillanic acid derivatives, their tendency to undergo dimerization and oxidation to colored by-products and degradation of the β-lactam ring in alkaline solutions renders the formation of alkali metal salts suitable for pharmaceutical usage without further purification difficult.

The alkali metal salts produced by the art described procedures are generally of poor quality as regards color of the salt. Solutions prepared therefrom are frequently of low stability as a result of auto-catalyzed degradation and ill-suited for the preparation of pharmaceutically elegant preparations required by the medical and pharmaceutical professions.

The formation of alkali metal salts of 6-acylamidopenicillanic acids, including those wherein the 6-acylamido group carries a basic substituent, e.g., an amino group as in 6-(α-aminophenylacetamido)-penicillanic acid (ampicillin) has, for example, been achieved by a process which comprises treating the ampicillin in an organic solvent with a primary or secondary aliphatic amine, a cycloaliphatic or heterocyclic amine to form an amine salt and then adding an alkali metal compound (methoxide, iodide, phenoxide, thiocyanate, ethyl sodio-acetate) to precipitate the alkali metal salt (British Pat. No. 1,128,235).

British Pat. No. 1,060,034 describes a process for preparing alkali metal salts of ampicillin by reacting the triethylamine salt of ampicillin in an organic solvent with an alkali metal alkoxide.

U.S. Pat. No. 3,669,957 discloses the preparation of sodium ampicillin by reaction of the diethylamine salt of ampicillin in methylene chloride solution with sodium 2-ethylhexanoate and subsequent precipitation of the sodium salt by addition of acetonitrile to the solution.

SUMMARY OF THE INVENTION

It has now been found that high quality alkali metal salts of 6-[2-phenyl-2-(imidoylaminoalkanoylamino)acetamido]penicillanic acids can be prepared by a simple, convenient and economical process which comprises treating a solution of an amine salt of the penicillanic acid compound in an organic solvent with a solution of an appropriate alkali metal salt dissolved in an organic solvent.

The 6-[2-phenyl-2-(imidoylaminoalkanoylamino)acetamido]penicillanic acids have the formula

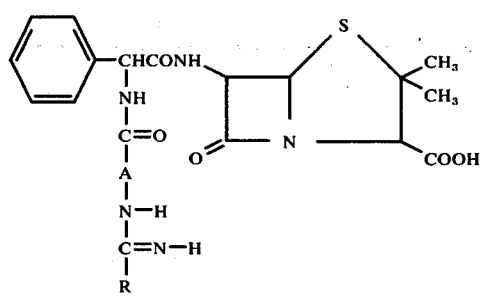

wherein
A is selected from the group consisting of methylene and alkylidene containing from 2 to 3 carbon atoms; and
R is selected from the group consisting of pyridyl; pyrimidinyl; pyridazinyl; pyrazinyl; benzimidazolyl; pyrryl; 2-pyrrolinyl; picolyl; substituted pyridyl wherein said substituent is selected from the group consisting of fluoro, chloro, bromo, and 2,6-dichloro; and pyridyl-1-oxide.

The term "alkali metal salt" is intended to include sodium and potassium salts. Suitable alkali metal salts are the alkali metal iodides, alkoxides, especially those having from one to four carbon atoms, phenoxides, thiocyanates, alkanoates having from two to eight carbon atoms and alkyl acetoacetates especially those having from one to four carbon atoms in the alkyl group.

DETAILED DESCRIPTION OF THE INVENTION

The process is conducted in a reaction-inert solvent medium which can be a single solvent or a mixture of solvents. It is necessary that the 6-[2-phenyl-2-(imidoylaminoalkanoylamino)acetamido]penicillanic acid amine salt dissolve substantially completely in the solvent medium in order to achieve a practical rate of reaction, essentially complete conversion to the alkali metal salt and an alkali metal salt of high quality. Therefore, depending upon the particular 6-[2-phenyl-2-(imidoylaminoalkanoylamino)acetamido]penicillanic acid amine salt and alkali metal salt used, a single solvent or a mixture of solvents can be used. In many instances a mixture of solvents is found to be best suited for the optimum conduct of this valuable process, one solvent for the amine salt and one for the alkali metal salt. When using a solvent medium comprising a mixture of solvents, the solvents should, for practical reasons of reaction rate and completeness of reaction, be miscible with one another in the proportions used.

The salt of the appropriate 6-[2-phenyl-2-(imidoylaminoalkanoylamino)acetamido]penicillanic acid can be preformed prior to dissolution in a suitable solvent or it can be formed in situ. In actual practice, as a matter of convenience and economy, it is preferred to form the amine salt in situ. The penicillanic acid compound is dissolved or suspended in the chosen solvent system; i.e., a single solvent or a mixture of solvents, and then treated with an excess of an appropriate amine.

Alternatively, the penicillanic acid compound is added to a solution of an appropriate amine. The amine is frequently, but not necessarily, added in the form of a solution in the same solvent in which the penicillanic acid reactant is dissolved or suspended. Suitable solvents are those organic solvents which completely dissolve the amine salt within a reasonable time and which afford a solution thereof about 5% or greater concentration. These requirements are dictated primarily for reasons of economy and practicality especially as regards large scale operation of the process. Suitable organic solvents are readily determined by simple experiment. Favored solvents are methylene chloride, tetrachloroethane and chloroform. Methylene chloride is a preferred solvent when the penicillanic acid reactant is used as its triethylamine salt.

A wide variety of amines are useful in the present process, including primary, secondary, and tertiary alkylamines having a total of at least six carbon atoms, and tertiary heterocyclic amines. The sole criterion is that the amines form a salt with the penicillanic acid reactant which is soluble in the solvent system used.

When using one of the above-enumerated solvents, tertiary alkylamines, such as triethylamine, tri-n-butylamine, ethyldiisopropylamine and tri-n-octylamine; N-alkylpiperidines such as N-ethylpiperidine; secondary amines such as di-n-octylamine and diheptylamine; and primary amines such as n-hexylamine and n-octylamine are especially useful for forming solvent soluble amine salts. The choice of a suitable organic solvent system and amine are readily determined by experiment.

The proportion of amine to penicillanic acid reactant used is not critical but can vary widely. It can range from about equimolar amounts up to a large excess of amine. The ratio actually used is a compromise of several factors, such as the rate of formation of the amine salt, the rate of solution of the amine salt, the solvent, the temperature and, of course, the amine and penicillanic acid reactants, and the concentrations thereof.

In actual practice molar ratios of amine to penicillanic acid reactant of from about 2 to about 18 or higher are useful in this process. Molar ratios below 2 generally require to long a time for solution of the penicillanic acid amine salt and are not practical for large scale operation.

The amine can be, but need not be, added as a solution in the same solvent in which the penicillanic acid reactant is dissolved or suspended since this facilitates amine salt formation. When the amine is added as a solution, concentrations of amine of from about 3-10% v/v in the solvent used are especially convenient for the practical conduct of this process.

The preferred amine is triethylamine for reasons of overall economy. It is readily available, affords satisfactory rate of solution of the penicillanic acid reactant and good yields of high quality alkali metal salts. The preferred solvent when using triethylamine is methylene chloride. Concentrations of 4-7% v/v triethylamine in methylene chloride are especially useful for forming the penicillanic acid amine salt when a ratio of triethylamine to penicillanic acid reactant of 2:1 is used. Salt formation occurs at a practical rate suitable for large scale operation under such conditions.

The alkali metal salt used is not critical to the process of this invention. The one criterion which it must fulfill is that it be sufficiently soluble in the solvent system in which the reaction with amine salt is to occur to permit the exchange to take place. This is, of course, readily determined by experiment. Suitable alkali metal salts are those enumerated above.

The alkali metal is added to the amine salt solution in the form of an organic solution thereof. As noted above, the solvent can be the same, or a different, solvent from that used to solubilize the amine salt. It can, if necessary, be a mixture of solvents. When a solvent different from that used to solubilize the amine is employed, the solvent chosen should be miscible with that used to dissolve the amine salt as noted above.

It is also essential that the alkali metal salt reactant not precipitate when added to the amine salt solution. This, of course, is a function of the solvents used, the concentrations of reactants and temperature, and is readily determinable by experiment.

The alkali metal salt is used in equimolar or essentially equimolar ratio to the penicillanic acid reactant. Higher or lower proportions tend to reduce the purity of the salt produced. Isopropyl alcohol is a favored solvent when an alkali metal iodide is used as source of the alkali metal ion. A 2:1 mixture of chloroform: ethyl acetate is a favored solvent system when an alkali metal 2-ethyl hexanoate is used as alkali metal ion source. When using an alkali metal alkoxide as alkali metal ion source, a 1:1 mixture of methanol:isopropyl alcohol is favored.

When using an alkali metal iodide as reactant it is desirable, in order to minimize degradation of the iodide and subsequent contamination of the alkali metal salt product with iodine, to deaerate the solvents used. This is conveniently accomplished by bubbling nitrogen gas through the solvents prior to introduction of the alkali metal iodide.

The reaction is conducted at a temperature of from −10° C. to 50° C. and desirably at from 0° C. to 50° C. The preferred temperature range is from 10° C. to 30° C.

In a preferred form of this process, a solution of the triethylamine salt of the 6-[2-phenyl-2-(imidoylaminoalkanoylamino)acetamido]penicillanic acid in deaerated methylene chloride is treated with a deaerated isopropyl alcohol solution of sodium iodide at 0° to 30° C. The sodium salt which precipitates is recovered by filtration.

The presence of up to 5% water can be tolerated during operation of the process. However, in order to facilitate maximum precipitation of the alkali metal salts and to minimize decomposition of the product it is preferred to conduct the process under anhydrous or essentially anhydrous conditions. Water, when present, is conveniently removed or reduced in concentration, if desired, by treating the amine salt solution with a suitable drying agent such as sodium sulfate or magnesium sulfate.

EXAMPLE 1

Sodium 6-[2-Phenyl-2-(4-Pyridylimidoylaminoacetamido)Acetamido] Penicillanate

To a solution of triethylamine (218 ml., 1.590 mol) in methylene chloride (750 ml., dried over $MgSO_4$ and deaerated) is added with stirring 6-[2-phenyl-2-(4-pyridylimidoylaminoacetamido)acetamido]penicillanic acid (44.8g., 0.0878 mol) in 5 gram portions. The penicillanic acid reactant dissolves quickly and addition requires about five minutes. The clear, light brown solution is dried with anhydrous sodium sulfate (300g.) for a half-hour and is then filtered. The filter cake is washed with methylene chloride (3 × 100 ml. of deaerated) and the combined filtrate and washings filtered through a millipore filter and collected in a 3-neck flask equipped with mechanical stirrer, addition funnel and drying tube.

A solution of sodium iodide in isopropanol (prepared by dissolving 12.17g., 0.08118 mol. NaI in 150 ml. of deaerated isopropanol under a $N_2$ atmosphere and filtering under $N_2$ through a sintered glass funnel) is added dropwise over a period of 23 minutes via the dropping funnel to the penicillanic acid amine salt. Precipitation of the sodium salt occurs immediately upon addition of the sodium iodide solution. The reaction mixture is stirred for 2.5 hours and the sodium salt recovered by filtration. The filter cake is washed with methylene chloride (500 ml.) and partially dried on the funnel under nitrogen for a half-hour. The cake is then slurried in dry methylene chloride (1500 ml.) for one hour, filtered and the cake reslurried in methylene chloride (1500 ml.) for two hours. It is then filtered and dried overnight on the funnel under nitrogen. Yield= 39.2g. of white solid. M.P. sinters at 218°–223° C; decomposes at 223°–227° C.

EXAMPLE 2

Sodium 6-[2-Phenyl-2-(4-Pyridylimidoylaminoacetamido)Acetamido]Penicillanate

6-[2-phenyl-2-(4-pyridylimidoylaminoacetamido)acetamido]penicillanic acid (2.55g., 5 mmol) is added portionwise (250 mg. portions) over 15 minutes to a solution of triethylamine (8.3 ml.) in dry methylene chloride (75 ml., dried with $MgSO_4$) at ambient temperature. The resulting solution is stirred for a half-hour and then dried using $Na_2SO_4$ (25 g.). The sodium sulfate is removed by filtration and the filter cake washed with dry methylene chloride (2 × 25 ml.). To the combined filtrate and washings is then added 15 ml. of 0.33M sodium 2-ethylhexanoate (in chloroform/ethyl acetate. 2:1 v/v) dropwise over a 5 minute period. Immediate precipitation of the sodium salt occurs. The suspension is stirred for 2 hours and then filtered. The product is slurried in methylene chloride (60 ml.) for 3 hours, filtered and the slurry step repeated. It is then slurried in chloroform (100 ml.) for two hours followed by a further slurry in ethyl acetate (100 ml.) overnight. The solid is filtered, washed with ethyl acetate (2 × 30 ml.) and dried under nitrogen.

The above procedure is repeated but using the appropriate alkali metal alkanoate or alkali metal alkyl acetoacetate in place of sodium 2-ethylhexanoate to produce the corresponding alkali metal salts.

| Alkali Metal Alkanoates | |
|---|---|
| sodium acetate | potassium acetate |
| sodium butyrate | potassium propionate |
| sodium caproate | potassium n-valerate |
| sodium caprylate | potassium 2-ethylhexanoate |

| Alkali Metal AlkylAcetoacetates ($CH_3COCHCOOR'$)M | | | |
|---|---|---|---|
| M | R | M | R |
| Na | $CH_3$ | K | $CH_3$ |
| Na | $C_2H_5$ | K | $C_2H_5$ |
| Na | $n-C_4H_9$ | K | $n-C_3H_7$ |

EXAMPLE 3

Sodium 6-[2-Phenyl-2-(4-Pyridylimidoylaminoacetamido)Acetamido]Penicillanate

To a solution of triethylamine (4.9 ml.. 0.036 mol) in dry methylene chloride (75 ml.) is added 6-[2-phenyl-2-(4-pyridylimidoylaminoacetamido)acetamido]-penicillanic acid (1.035g., 0.002 mol.) over a two minute period. A solution of sodium methoxide (1.0007g., 0.0019 mol) in methanol/isopropanol (10 ml. of 1:1) is then added with stirring. Immediate precipitation of the desired sodium salt occurs. The mixture is stirred for two hours and then filtered. The filter cake is washed with methylene chloride (2 × 15 ml.) and dried under nitrogen. Yield = 0.732g.

Repetition of this procedure but using the following alkali metal alkoxides affords the corresponding alkali metal salts:
sodium ethoxide
sodium propoxide
sodium n-butoxide
potassium methoxide
potassium n-butoxide

EXAMPLE 4

The procedure of Example 3 is repeated but using an equivalent amount of sodium iodide in isopropanol (15 ml.) in place of sodium methoxide as source of sodium and equivalent amounts of the amines listed below in place of triethylamine.

| Amine | Yield of Sodium Salt |
|---|---|
| ethyldiisopropylamine | 0.85g. |
| tri-n-octylamine | 0.87g. |
| diheptylamine | 0.93g. |
| N-ethylpiperidine | 0.43g.* |

*Used ½ quantities reported in Example 3.

EXAMPLE 5

Sodium 6-[2-Phenyl-2-(4-Pyridylimidoylaminoacetamido)Acetamido]Penicillanate

To a solution of triethylamine (4.9 ml., 0.036 mol) in dry methylene chloride (75 ml.) is added 6-[2-phenyl-2-(4-pyridylimidoylaminoacetamido)acetamido]-penicillanic acid (1.035g., 0.002 mol.) over a two-minute period. A solution of sodium phenoxide (0.218g. 0.0019 mol) in isopropanol (15 ml.) is then added with stirring. Immediate precipitation of the desired sodium salt occurs. The mixture is stirred for two hours and then filtered. The filter cake is washed with methylene chloride (30 ml.) and then slurried for one hour in methylene chloride (50 ml.). The slurry is filtered, the filter cake washed with methylene chloride (2 × 20 ml.) and dried under nitrogen. Yield = 0.68 g.

In like manner, substitution of potassium phenoxide for sodium phenoxide in the above procedure provides the corresponding potassium salt.

EXAMPLE 6

Potassium 6-[2-Phenyl-2-(4-Pyridylimidoylaminoacetamido)Acetamido]Penicillanate

To a solution of triethylamine (4.9 ml.) 0.036 mol) in dry, deaerated methylene chloride (75 ml.) is added 6-[2-phenyl-2-(4-pyridylimidoylaminoacetamido) acetamido]penicillanic acid (1.035 g., 0.002 mol.) over a two-minute period. A solution of potassium iodide (0.31 g., 0.0019 mol) in deaerated methanol (5 ml.) is then added with stirring. Immediate precipitation of the desired potassium salt occurs. The mixture is stirred for two hours and then filtered. The filter cake is washed with methylene chloride (2 × 25 ml.) and dried under nitrogen. Yield = 0.89g. M.P. 212°–215° C. (dec.).

Repetition of this procedure but substituting triethylamine by equivalent amounts of n-hexylamine, N-n-butyl piperidine, n-decylamine and di-n-octylamine affords the same product.

EXAMPLE 7

Potassium 6-[2-Phenyl-2-(4-Pyridylimidoylaminoacetamido)Acetamido]Penicillanate

Repetition of the procedure of Example 6, but substituting potassium thiocyanate (0.184g.) in methanol (7 ml.)/isopropanol (3 ml.) solution for potassium iodide in methanol affords the title product.

Similarly, substitution of sodium thiocyanate for potassium thiocyanate in the above procedure affords the corresponding sodium salt.

EXAMPLE 8

Repetition of the procedures of Examples 1 and 6 but using an equimolar amount of the appropriate 6-[2-phenyl-2-imidoylaminoalkanoylaminoacetamido] penicillanic acid in place of 6-[2-phenyl-2-(4-pyridylimidoylaminoacetamido) acetamido]penicillanic acid affords the sodium and potassium salts of the following compounds:

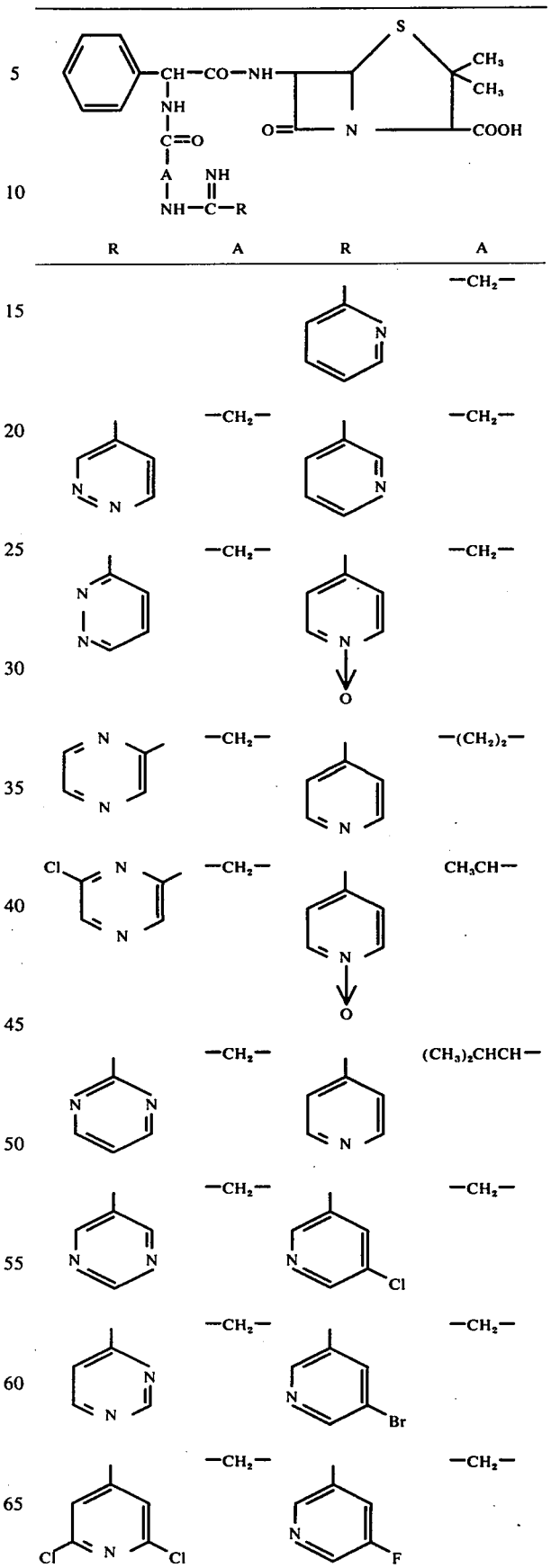

-continued

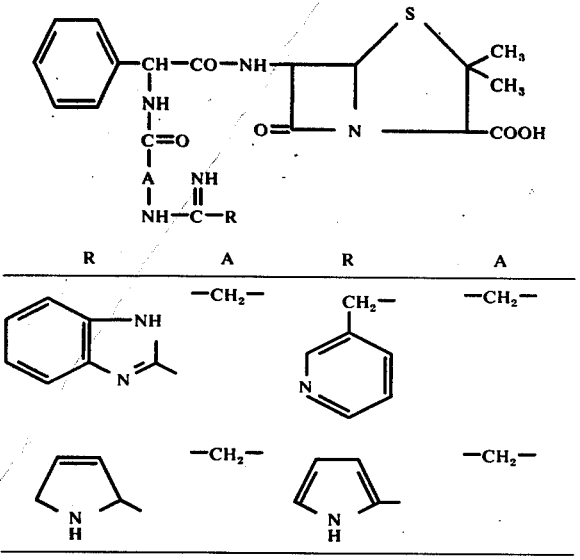

What is claimed is:

1. A process for the preparation of alkali metal salts of 6-[2-phenyl-2-(imidoylaminoalkanoylamino)acetamido]penicillanic acids which comprises treating a primary, secondary or tertiary amine salt of said penicillanic acid, said amine having a total of at least six carbon atoms, in a reaction inert solvent with an alkali metal salt selected from the group consisting of alkali metal iodides, phenoxides, alkoxides having from one to four carbon atoms, thiocyanates, alkanoates having from two to eight carbon atoms in the alkyl group and alkyl acetoacetates having from 1 to 4 carbon atoms in the alkyl group.

2. A process for the preparation of alkali metal salts of 6-[2-phenyl-2-(imidoylaminoalkanoylamino)acetamido]penicillanic acids which comprises:

Admixing a 6-[2-phenyl-2-(imidoylaminoalkanoylamino)acetamido]penicillanic acid with a primary, secondary, or tertiary amine in a reaction-inert solvent to form a solution of the amine salt of the penicillanic acid;

Admixing the said solution with a solution in a reaction-inert solvent of an alkali metal salt selected from the group consisting of alkali metal iodides, phenoxides, alkoxides having from one to four carbon atoms, thiocyanates, alkanoates having from two to eight carbon atoms and alkyl acetoacetates having from one to four carbon atoms in the alkyl group.

3. The process according to claim 2 wherein the 6-[2-phenyl-2-(imidoylaminoalkanoylamino)acetamido]penicillanic acid has the formula

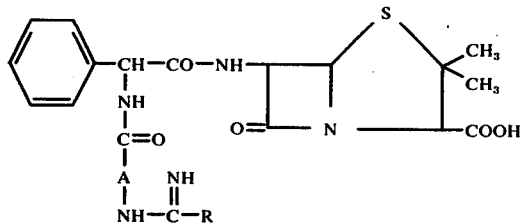

wherein

A is selected from the group consisting of methylene and alkylidene containing from 2 to 3 carbon atoms; and R is selected from the group consisting of pyridyl, pyrimidinyl, pyridazinyl, pyrazinyl, benzimidazolyl, pyrryl, 2-pyrrolinyl, picolyl, substituted pyridyl wherein said substituent is selected from the group consisting of fluoro, chloro, bromo, and 2,6-dichloro; and pyridyl-1-oxide.

4. The process according to claim 3 wherein the alkali metal salt is an alkali metal iodide.

5. The process according to claim 4 wherein the amine is triethylamine.

6. The process according to claim 5 wherein A is methylene.

7. The process according to claim 6 wherein R is 4-pyridyl.

8. The process according to claim 7 wherein the alkali metal iodide is sodium iodide.

* * * * *